United States Patent [19]

Meuzelaar

[11] 4,408,125

[45] Oct. 4, 1983

[54] MODULAR PYROLYSIS INLET AND METHOD FOR PYROLYZING COMPOUNDS FOR ANALYSIS BY MASS SPECTROMETER

[75] Inventor: Hendrik L. C. Meuzelaar, Summit Park, Utah

[73] Assignee: University of Utah, Salt Lake City, Utah

[21] Appl. No.: 282,789

[22] Filed: Jul. 13, 1981

[51] Int. Cl.$^3$ ............................................. H01J 49/04
[52] U.S. Cl. .................................................... 250/288
[58] Field of Search ............................... 250/288, 425

[56] References Cited

PUBLICATIONS

"Versatile Mass Spectrometric Inlet System for High Boiling Liquid Samples and for Thermoanalysis of Nonvolatile Materials"; Shen et al.; *Analytical Chemistry*, vol. 48, No. 14, pp. 2291–2292, Dec. 1976.

"Pyrolysis Mass Spectrometry; Prospects for Interlaboratory Standardization," H. L. C. Meuzelaar, Proc. 26th ASMS Conf. of Mass Spectrom. All. Topics, St. Louis, pp. 29–41, (1978).

"A Technique for Fast and Reproduceable Fingerprinting of Bacteria by Pyrolysis Mass Spectrometry"; Meuzelaar, H. L. C. et al.; Anal. Chem., 45, 587–590, (1973).

"Beitrag zur Curie-punkt-pyrolyse/massenspektrometrie Organischer Verbindungen," Oertli, C. U., Ph.D. Thesis, Eidgenossischen Technischen Hochschule, Zurich, Switzerland, (1974).

"Recent Advances in Pyrolysis Mass Spectrometry of Complex Biological Materials," H. L. C. Meuzelaar et al., Biomed. Mass Spectrom, 1, 312–319, (1974).

"Automated Pyrolysis Mass Spectrometry; Application to the Differentiation of Microorganisms," H. L. C. Meuzelaar et al., Advances in Mass Spectrometry, vol. 7B, ed. N. R. Daly, Heyden and Son, London, pp. 1452–1456, (1976).

*Primary Examiner*—Alfred E. Smith
*Assistant Examiner*—Jack I. Berman
*Attorney, Agent, or Firm*—H. Ross Workman; Allen R. Jensen; Dale E. Hulse

[57] ABSTRACT

A modular pyrolysis inlet apparatus and method for pyrolyzing compounds preparatory to an analysis thereof by a mass spectrometer. The pyrolysis inlet includes a telescopic insertion probe having a ferromagnetic wire bearing the sample to be analyzed, and a reaction chamber mounted to the insertion probe so as to encompass the wire and sample. The insertion probe/reaction chamber assembly is inserted into the pyrolysis inlet apparatus and the voids surrounding the assembly are evacuated. The sample is cooled at a first position within the reaction chamber while a heating mantle preheats the reaction chamber at a second position therein. The telescopic insertion probe/reaction chamber assembly is then inserted further into the pyrolysis inlet, moving the sample to the second heated position within the reaction chamber. At the second position, a high frequency coil is activated to energize and heat the wire, and rapidly pyrolyze the sample thereon. The volatile pyrolysis products escape from the reaction chamber and enter a modular expansion chamber. The volatile pyrolysis products are delayed for a moment within the expansion chamber and then introduced directly into a mass spectrometer for subsequent analysis.

39 Claims, 4 Drawing Figures

MODULAR PYROLYSIS INLET AND METHOD FOR PYROLYZING COMPOUNDS FOR ANALYSIS BY MASS SPECTROMETER

BACKGROUND

1. The Field of the Invention

The present invention relates to a method and apparatus for the analysis of chemical compounds, and more particularly, to a novel method and apparatus for pyrolyzing compounds preliminary to analysis in a mass spectrometer.

2. The Prior Art

Many scientific techniques have been developed for the identification of chemical compounds; they include, for example, mass spectrometry, gas-liquid chromatography, infrared spectrometry, and nuclear magnetic resonance spectrometry. It is difficult, however, to use such techniques for the identification or "fingerprinting" of complex macromolecular materials.

One method advanced for fingerprinting such complex compounds is pyrolysis gas-liquid chromatography ("Py-GLC"). In the Py-GLC method, the sample to be analyzed is first "pyrolyzed" (i.e., chemically decomposed by heat) before being introduced into the gas-liquid chromatograph. The products resulting from pyrolysis are usually of lower molecular weight than the original macromolecular structure of the sample, and are, therefore, more easily analyzed by the gas-liquid chromatographer.

Although significant progress has been made in the development of Py-GLC techniques during recent years, the usefulness of these techniques for the fingerprinting of organic solids and other complex materials is still considerably limited by a lack of standardization and interlaboratory reproducibility. The reproducibility problems encountered are due primarily to the practical imperfections of gas chromatography rather than to problems associated with the pyrolysis techniques. For example, such factors as insufficient column resolution, gradual deterioration of column performance, or sudden differences introduced by column replacement have heretofore posed formidable obstacles to the computer processing of Py-GLC data and the compilation of reference libraries of standard fingerprints.

The need for reproducible fingerprints of complex biological and geochemical materials has thus led some to explore the technique of pyrolysis mass spectrometry. Using this technique, a sample having a complex macromolecular structure is first pyrolyzed to break the structure down into lower molecular weight, volatile fragments characteristic of the original structure. These fragments are then ionized and analyzed by mass spectrometric techniques.

The repeatability of pyrolysis fragmentation patterns is, among other considerations, determined by the reproducibility of the temperature rise profile while heating the sample, and the maximum temperature at which pyrolysis occurs. These parameters can be standardized by using ferromagnetic wires to hold the sample and energizing a high frequency coil to heat the wire to its Curie-point. At the Curie-point of the ferromagnetic wire, the disappearance of the ferromagnetic properties of the wire stabilizes the maximum wire temperature. Such a Curie point technique thus begins to solve some of the problems associated in obtaining the reproducibility needed for identification purposes.

Although recent developments in pyrolysis mass spectrometry have eliminated some of the problems associated with pyrolysis gas-liquid chromatography, significant problems are still encountered during the pyrolysis phase of the pyrolysis mass spectrometric technique. For example, due to the high reaction chamber wall temperatures needed to prevent condensation losses of pyrolysis products, premature thermal damage to the sample may occur before pyrolysis can be performed. As a result, a different mixture of pyrolysis products is obtained which is less characteristic of the original sample. Furthermore, the ill-defined nature of the thermal damage to the sample aggravates reproducibility problems.

In order to avoid the problem of premature heating, most Curie-point pyrolysis studies use relatively cold reaction chamber walls. However, this creates another problem, namely the loss of less volatile pyrolysis products. Immediately after pyrolysis of the high molecular weight sample, the less volatile components of the pyrolyzed sample condense on the relatively cold walls of the reaction chamber. Thus, these less volatile components remain within the reaction chamber and are not subsequently analyzed by the mass spectrometer. Not only does this problem render the resultant mass spectrum incomplete, but it also contaminates the reaction chamber so that subsequent sample analyses may be inaccurate.

Moreover, both the effects of premature sample heating and of condensation losses on the reaction chamber walls may change from sample to sample. Hence, the reproduibility of the spectra obtained from the mass spectrometer is greatly impaired, and standardization of the spectra for subsequent identification referencing becomes difficult. It will be readily appreciated that the loss or change of components in the mass spectra creates missing pieces in the puzzle for determining the overall structural composition of the material analyzed. If this problem were eliminated, mass spectrometric analysis would provide a better description of the entire macromolecular structure, thus aiding the scientist in deducing both the chemical elements present and the structural composition of the analyzed sample.

A further problem associated with the various apparatus implementing the pyrolysis phase of pyrolysis mass spectrometry is that generally, each apparatus employs one fixed mode of limited application. For example, one typical pyrolysis/mass spectrometer employs only the rapid heating mode described above. In this type of apparatus, the sample is placed on a ferromagnetic wire which is heated by induction to pyrolyze the sample. In another apparatus, the sample is introduced into a reaction chamber and heated gradually until chemical decomposition of the sample is achieved. This mode is often referred to as "direct probe" or "oven pyrolysis." Still another apparatus pyrolyzes the sample by means of a laser beam.

Additionally, pyrolysis mass spectrometers employ different techniques for introducing the decomposed components of the sample into the mass spectrometer for analysis. In one apparatus, an expansion chamber is positioned between the pyrolysis reaction chamber and the mass spectrometer to delay passage of the pyrolyzed products into the mass spectrometer and thus obtain one mass spectrum of the entire pyrolyzed sample. Another pyrolysis mass spectrometer has no such expansion chamber—pyrolysis of the sample being achieved directly in front of the ion source of the mass spectrome-

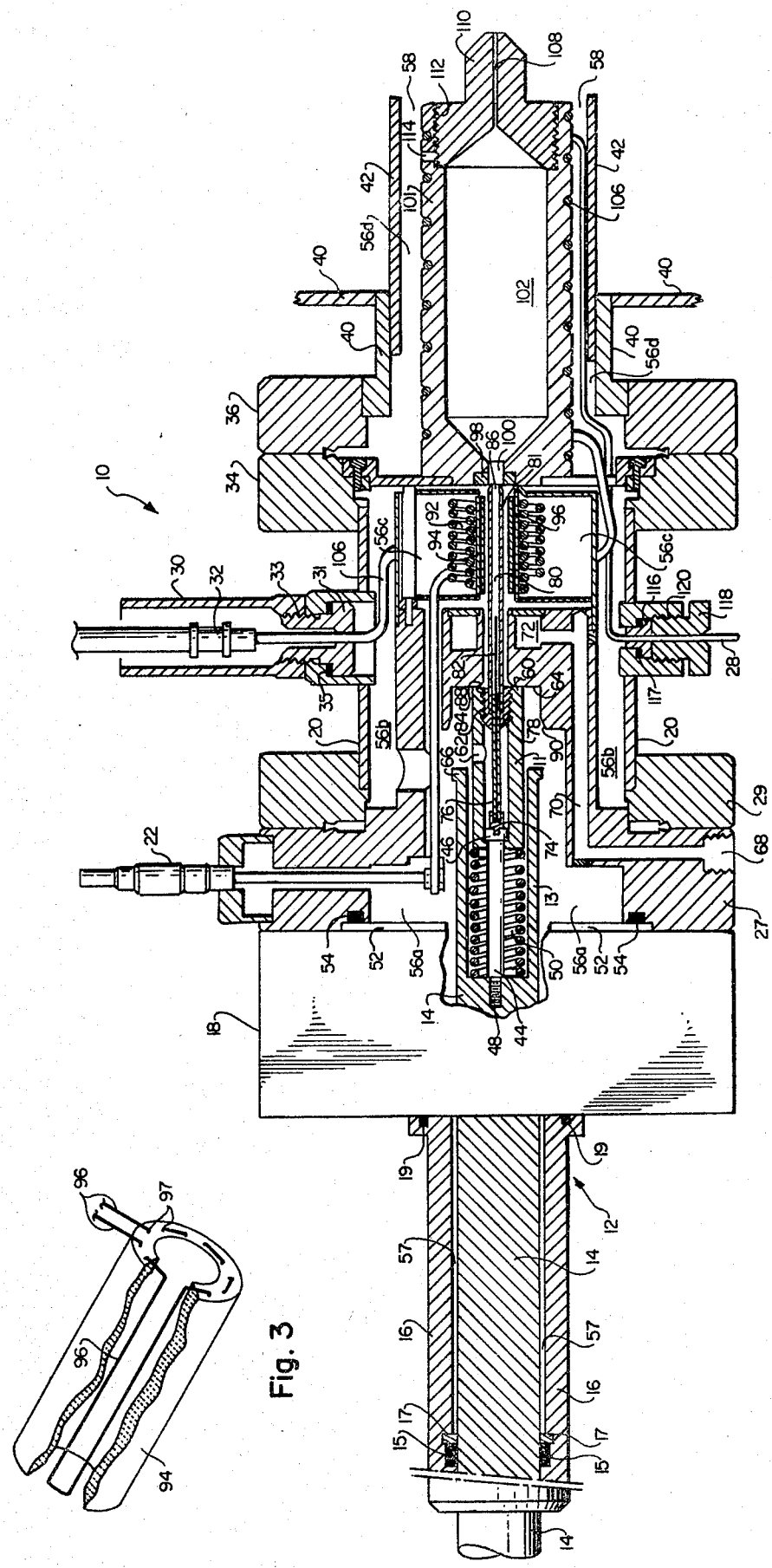
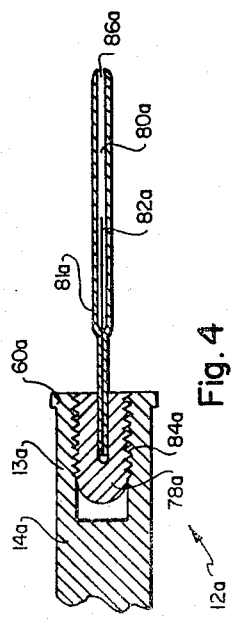
Fig. 2
Fig. 3
Fig. 4 ter. This type of pyrolysis apparatus allows the scientist to obtain mass spectra of the individual components of the pyrolyzed sample produced at different times during pyrolysis, since the volatile pyrolysis products are not mixed and delayed in an expansion chamber. However, highly volatile components produced in this type of pyrolysis apparatus often escape analysis by the mass spectrometer due to the minimum response time required by the mass spectrometer for analysis thereof.

Thus, the pyrolysis mass spectrometers existing in the art are generally each capable of implementing only one mode of pyrolysis—the heating and pyrolysis product introducing features being fixed and invariable.

In view of the foregoing, it would be a significant advancement in the art to provide a pyrolysis inlet for a mass spectrometer that would protect the sample from thermal damage prior to pyrolysis while pyrolyzing high molecular compounds without significant condensation of low volatile pyrolysis products on the reaction chamber walls. Additionally, it would be another desirable advancement in the art to provide a pyrolysis inlet for a mass spectrometer which is capable of implementing several pyrolysis modes, as well as sample introduction modes, into a single apparatus. Such an invention is disclosed and claimed herein.

BRIEF SUMMARY AND OBJECTS OF THE INVENTION

The present invention comprises a method and apparatus for pyrolyzing a sample preparatory to analysis by a mass spectrometer. The pyrolysis inlet is modular in that it can be mounted directly to the mass spectrometer for use when pyrolysis is desirable (e.g., when the sample has a very high molecular weight) but can be subsequently removed from the mass spectrometer when pyrolysis is not needed (e.g., when simple compounds are being analyzed).

The modular pyrolysis inlet of the present invention includes a telescopic insertion probe having a ferromagnetic wire for bearing the sample to be pyrolyzed and a reaction chamber mounted to the insertion probe so as to enclose the ferromagnetic wire and sample. When the telescopic insertion probe/reaction chamber assembly is inserted into the pyrolysis inlet apparatus, the voids surrounding the insertion probe/reaction chamber assembly are evacuated. Subsequently, the sample-bearing end of the wire is disposed at a first position within the reaction chamber. The portion of the reaction chamber immediately surrounding the sample at the first position therein is cooled so as to prevent thermal damage to the sample prior to pyrolysis. Simultaneously, the most forward part of the reaction chamber, not yet surrounding the sample, is heated up to a temperature suitable to prevent condensation losses of pyrolysis products when the sample will be pyrolyzed.

Subsequently, the telescopic configuration of the insertion probe permits rapid positioning of the ferromagnetic wire and sample in the most forward, preheated part of the reaction chamber. In this position, a high frequency coil immediately energizes the ferromagnetic wire so as to rapidly heat and pyrolyze the sample before thermal damage by radiation from the preheated walls can occur.

The modular pyrolysis inlet incorporates each of the prior art modes of operation plus several additional modes into a single apparatus. In conjunction with the rapid heating mode described above, a heating mantle positioned between a portion of the reaction chamber and the high frequency coil can be used to preheat the reaction chamber at its second position while the sample is being cooled at the first position. Therefore, upon introduction of the sample at the second position, the high frequency coil is energized to pyrolyze the sample with minimal condensation of pyrolysis products on the reaction chamber walls since the walls were preheated prior to pyrolysis.

The pyrolysis inlet apparatus can also be used without energizing the high frequency coil by using the heating mantle alone to perform "oven pyrolysis." The inlet design of the present application also allows for pyrolysis of the sample by a laser, which is activated to irradiate the sample at the second position within the reaction chamber. In addition, the modular pyrolysis inlet can also be used with a combination mass spectrometer/mass spectrometer which isolates a selected ion species of the ionized pyrolysis products in the first mass spectrometer for a specialized analysis thereof in the second mass spectrometer.

In the present invention, a modular expansion chamber is positioned between the reaction chamber and the mass spectrometer to mix the pyrolysis products and delay their entry into the mass spectrometer. Alternatively, the expansion chamber may be removed, and the reaction chamber placed directly in front of the ion source of the mass spectrometer to perform a direct probe analysis. Thus, the modular pyrolysis inlet apparatus of the present invention incorporates many different modes of operation in the same apparatus, some of which were previously unknown in the art.

It is, therefore, an object of the present invention to provide a modular pyrolysis inlet for a mass spectrometer which can be mounted to the mass spectrometer for use with or without expansion chamber, and subsequently removed when it is desired to use the mass spectrometer alone.

It is another object of the present invention to provide a pyrolysis inlet for a mass spectrometer which prevents thermal damage to the sample prior to pyrolysis while minimizing condensation of low volatility pyrolysis products within the pyrolysis inlet, thereby providing complete analysis of both simple compounds and complex macromolecular compounds, such as biopolymers and geopolymers.

A further object of the present invention is to provide a pyrolysis inlet for a mass spectrometer which incorporates several pyrolysis modes into a single apparatus.

A still further object of the present invention is to provide a pyrolysis mass spectrometer with excellent reproducibility of results, permitting library cataloging of spectra for subsequent comparison and identification purposes.

Yet another object of the present invention is to provide a novel method of pyrolyzing compounds preparatory to their analysis by a mass spectrometer.

These and other objects and features of the present invention will become more fully apparent from the following description and appended claims taken in conjunction with the accompanying drawings.

BRIEF DESCRIPTION OF THE DRAWINGS

FIG. 2 is a partial cross-sectional view of the embodiment of FIG. 1 showing in detail the operational features of the modular pyrolysis inlet;

FIG. 3 is a perspective transparent view of one side of the heating mantle of the embodiment of FIGS. 1 and 2, the opposing side thereof being illustrated by dashed lines for the sake of clarity; and FIG. 4 is a cross-sectional view of a non-telescoping insertion probe/reaction chamber assembly of a second preferred embodiment of the modular pyrolysis inlet.

DETAILED DESCRIPTION OF THE INVENTION

Figure 1:
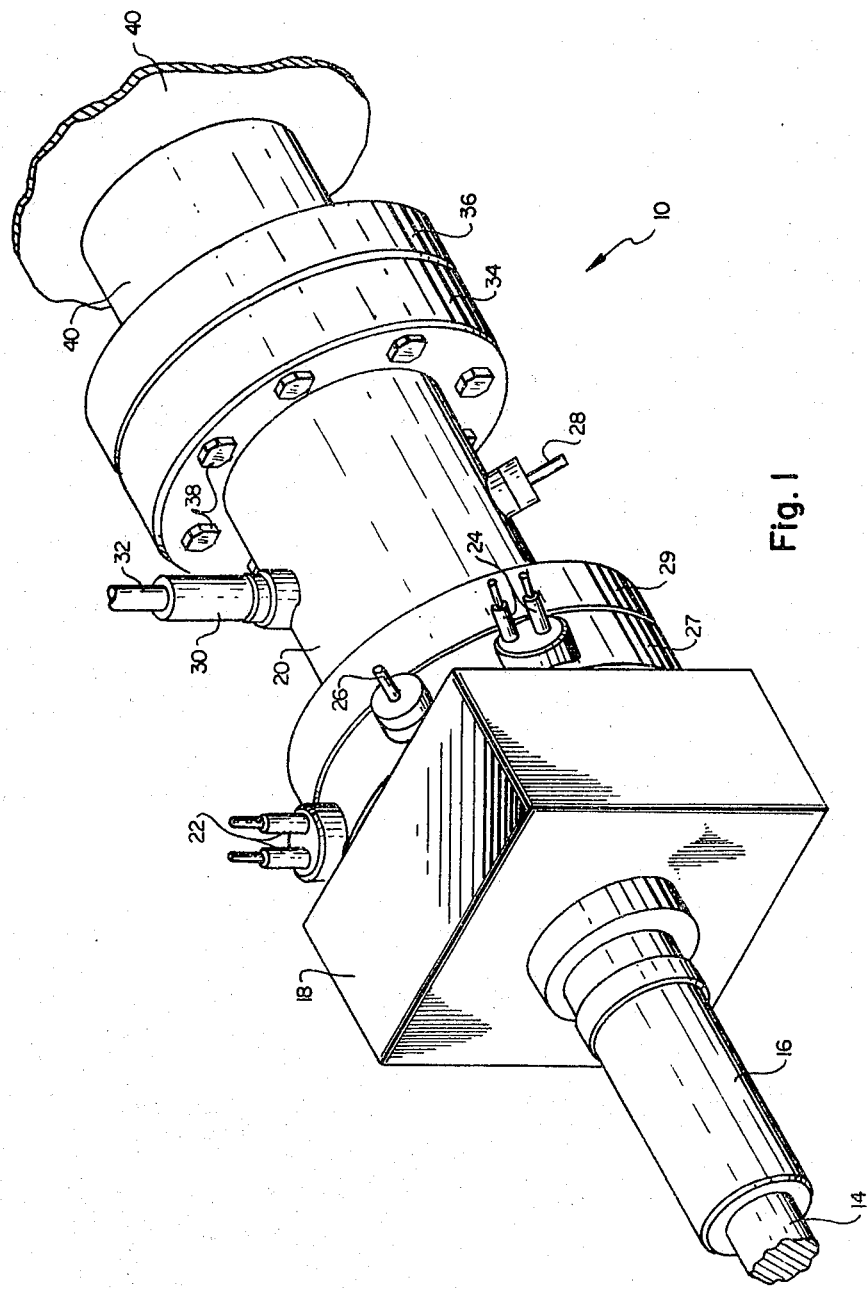
FIG. 1 is a perspective view of a first preferred embodiment of the modular pyrolysis inlet for a mass spectrometer of the present invention mounted to the mass spectrometer, illustrating primarily the configuration of the housing of the modular pyrolysis inlet.

Reference is now made to the figures wherein like parts are represented by like numerals throughout.

The modular pyrolysis inlet of the present invention, generally designated 10, is illustrated in FIGS. 1 and 2. FIG. 1 illustrates the general configuration of the housing of pyrolysis inlet 10, and FIG. 2 illustrates the detailed operational features of the pyrolysis inlet 10.

Referring to both FIGS. 1 and 2, pyrolysis inlet 10 includes an insertion probe generally designated 12. The insertion probe 12 comprises an insertion probe shaft 14 which is slidably insertable into an insertion probe housing 16. An O-ring 15 is placed adjacent the opening of housing 16 to provide a vacuum seal between probe shaft 14 and probe housing 16. A guide ring 17 is installed adjacent O-ring 15 so as to center the probe shaft 14 within probe housing 16.

The insertion probe housing 16 is mounted to a vacuum valve housing 18 with an O-ring 19 positioned therebetween to provide a vacuum seal. A three-way vacuum valve (not shown) located within vacuum valve housing 18 is in gaseous communication with a first standard vacuum pump (not shown). The vacuum valve can be selectively positioned to first allow evacuation of void 57 by the first vacuum pump, while preventing communication between void 57 and voids 56a–d within the apparatus. Subsequently, the vacuum valve can be positioned to shut off communication between the first vacuum pump and void 57, and allow communication between void 57 and voids 56a–d. As will be explained in more detail hereinafter, voids 56a–d are further evacuated by a second vacuum pump in communication with the mass spectrometer.

Vacuum valve housing 18 is connected to a pyrolysis chamber housing 20 by flanges 27 and 29. Vacuum valve housing 18 is mounted to flange 27 by a series of bolts (not shown) or other suitable attachment means. A centering guide 52 on vacuum valve housing 18 assures proper positioning of the vacuum valve housing with flange 27. Additionally, an O-ring 54, which acts as a vacuum seal, is positioned between centering guide 52 and flange 27. Flange 29 is welded to housing 20, and flanges 27 and 29 have a metal or elastomeric seal therebetween and are fastened together by a series of bolts (not shown).

Pyrolysis chamber housing 20 is connected to a mass spectrometer inlet housing 40 by flanges 34 and 36. Pyrolysis inlet flange 34 is welded to housing 20 and connected to mass spectrometer flange 36 by a metal or elastomeric seal and a plurality of bolts 38, in a manner similar to that used for flanges 27 and 29. Mass spectrometer inlet housing 40 is part of the housing of a typical commercially available mass spectrometer.

Referring more particularly to FIG. 2, insertion probe 12 further comprises a first telescoping member 11 and a second telescoping member 13, having ends 60 and 66, respectively. Second telescoping member 13 is formed as an extension of insertion probe shaft 14. First telescoping member 11 is slidably mounted to probe shaft 14 by a support bolt 44, which has a threaded portion 48 capable of threading into a recess formed in the end of probe shaft 14.

First telescoping member 11 has a hole formed in the bottom thereof to allow the shaft of bolt 44 to slidably pass through the interior of first telescoping member 11. As shown in FIG. 2, a head 46 on support bolt 44 prevents the shaft of bolt 44 from completely exiting first telescoping member 11. A spring 50 is coiled around the shaft of bolt 44 so as to provide tension between probe shaft 14 and first telescoping member 11 when the shaft of bolt 44 is slid into the interior of first telescoping member 11. First telescoping member 11 is provided with an evacuation port 62 to permit evacuation therein.

A ferromagnetic wire 82 transports the sample to be analyzed and is mounted within first telescoping member 11. Ferromagnetic wire 82 is inserted into a wire holder 76, which is positioned against support bolt 44 by means of a plastic or rubber cap 74. Ferromagnnetic wire 82 is made from such ferromagnetic materials as nickel, iron, and cobalt, having Curie-point temperatures of 358° C., 770° C., and 1128° C., respectively. By fabricating ferromagnetic wire 82 of these ferromagnetic metals or combined alloys thereof, ferromagnetic wire 82 can be made so as to have a precise Curie-point within a finely-spaced range of Curie-point temperatures from 358° C. to 1128° C.

Ferromagnetic wire 82 is positioned within a reaction chamber 80 formed by a reaction chamber wall 81. The reaction chamber wall is slidably inserted over the end of wire holder 76 such that feromagnetic wire 82 is disposed within reaction chamber 80. An elastomeric cap 78 is placed over the junction of wire holder 76 and reaction chamber wall 81 and is secured in place by threads 84 on first telescoping member 11. Cap 78 allows slidable movement of wire holder 76 within reaction chamber wall 81 and helps maintain proper alignment of ferromagnetic wire 82 within reaction chamber 80. Thus, the end of wire 82 can be slidably positioned at various locations within reaction chamber 80. Reaction chamber wall 81 is fabricated from a material capable of withstanding the pyrolysis temperatures; it is typically made of quartz or borosilicate glass. An outlet 86 is formed in the other end of reaction chamber wall 81 to allow the pyrolyzed sample to exit the reaction chamber.

Surrounding reaction chamber wall 81 is a heating mantle 94. As best viewed in FIG. 3, heating mantle 94 is cylindrically configurated having a heating filament 96 embedded therein. Heating mantle 94 can be made of machinable glass, such as Macor glass, or any other suitable material. Filament 96 is made of any suitable filament material, such as tungsten, and is preferably formed as a single loop within the heating mantle 94 in order to minimize the effect of the heating mantle upon the electromagnetic energy which is absorbed by ferromagnetic wire 82. Such minimal interference is accomplished by threading a single piece of tungsten wire through holes 97 in heating mantle 94 as shown in FIG. 3.

Referring now to FIGS. 1 and 2, electrical feedthroughs 24 carry an electric current, preferably direct current, to the tungsten filament 96 in order to heat filament 96. A thermocouple 26 is placed in communication with heating mantle 94 so as to measure the temperature of heating mantel 94. Generally, it is desirable to construct heating mantle 94 so it is capable of withstanding temperature up to 500° C.

A high frequency coil 92 is wound around the periphery of heating mantle 94 so as to encompass the heating mantle 94. Electrical feedthroughs 22 carry an electric current, preferably high frequency alternating current, to coil 92, thereby causing the coil to emit electromagnetic energy in the form of high frequency radio waves. This electromagnetic energy passes through heating mantle 94 and reaction chamber wall 8 and is absorbed by ferromagnetic wire 82 which is thereby heated quickly to its Curiepoint temperature. When the ferromagnetic wire 82 reaches its Curie-point temperature, the ferromagnetic properties of wire 82 disappear and the temperature of wire 82 quickly stabilizes.

Advantageously, heating mantle 94 and reaction chamber wall 81 are made of materials which allow passage of the radio waves from high frequency coil 92 to ferromagnetic wire 82 with minimal interference. Moreover, the low inductance of the single loop of tungsten wire forming heating mantle filament 96, as illustrated in FIG. 3, causes minimal interference with the high frequency radio waves emitted by high frequency coil 92 since the induction created by an electric current in filament 96 is proportional to the number of coil windings in the filament. The resultant lack of induction interference helps maintain standardization of the maximum temperature obtained by the ferromagnetic wire 82 at its Curie point.

The modular pyrolysis inlet 10 preferably further includes a water cooling system having a cooling reservoir 72 surrounding a portion of reaction chamber wall 81 and means for circulating water into pyrolysis inlet 10, through reservoir 72, and back out pyrolysis inlet 10. Water enters the pyrolysis inlet 10 though a water port 68 and is carried to the cooling reservoir 72 by a water duct 70. The water then circulates around reaction chamber wall 81 following a loop path, and exits pyrolysis inlet 10 through a corresponding water duct and water port (not shown). Water circulating through cooling reservoir 72 acts to cool a portion of the reaction chamber wall 81 nearest the cooling reservoir 72, thereby cooling reaction chamber 80.

A modular expansion chamber 102 is formed within an expansion chamber wall 101 having an inlet 100. Before insertion of reaction chamber wall 81 within the heating mantle, expansion chamber 102 is in gaseous communication with void 56c surrounding the high frequency coil 92. Upon complete insertion of reaction chamber wall 81 within the heating mantle 94, reaction chamber wall 81 contacts expansion chamber wall 101 at a seat 98 thereby allowing gaseous communication between reaction chamber 80 and expansion chamber inlet 100 and expansion chamber 102. An end cap 110 is threaded into the end of expansion chamber wall 101 opposite inlet 100 by means of threads 112. End cap 110 has a narrow expansion chamber outlet port 108 to provide gaseous communication between expansion chamber 102 and the mass spectrometer. To permit evacuation of air around threads 112, an evacuation port 114 is formed in expansion chamber wall 101.

Expansion chamber 102 is heated by a heating element 106 coiled around expansion chamber wall 101. Heating element 106 is heated by an electrical power supply 32 contained within a housing 30. Housing 30 is secured to housing 20 by a plug 31 having threads 33 corresponding to a threaded end of housing 30. An O-ring 35 is placed around plug 31 to provide for vacuum sealing. A heat shield 42 reflects radiant heat energy emitted by heating element 106 and expansion chamber wall 101 back towards expansion chamber wall 101, thus substantially increasing the efficiency of heating element 106.

A thermocouple 28 is placed in communication with expansion chamber wall 101 to measure the temperature of expansion chamber wall 101. Thermocouple 28 is mounted to housing 20 through a cap 118 having threads 120; thermocouple cap 118 is threadably inserted into housing 20 until it contacts a plug 116. An O-ring 117 provides a vacuum seal around plug 116.

Expansion chamber wall 101 and heat shield 42 form a vacuum port 58 to permit evacuation of voids 56a–d. A second conventional vacuum pump (not shown) is used to evacuate the mass spectrometer, and correspondingly, voids 56a–d through vacuum port 58.

The operation of the presently preferred embodiment of modular pyrolysis inlet 10 of the present invention in combination with a mass spectrometer for analysis of chemical samples is accomplished as follows. A sample is prepared by taking microgram quantities of the chemical composition to be analyzed (whether a solid, liquid or gas) and dissolving or suspending the composition in an appropriate solvent. As will be readily recognized by those of ordinary skill in the art, the selection of an appropriate solvent will depend largely upon the chemical nature of the material to be analyzed. Solvents such as methanol, water, saline solutions, benzene, acetone, buffered solutions, and carbon disulfide have been found to be useful in the preparation of different types of samples.

Insertion probe 12 is initially adjusted to its most extended position—the head 46 of bolt 44 resting squarely against the bottom side of first telescoping member 11. The ferromagnetic wire 82 is then inserted into wire holder 76 of the insertion probe. Ferromagnetic wire 82 is then contacted with the prepared sample so that a portion of the sample clings to the end thereof. The amount of sample (which may be suspended in solvent) required for analysis is so minute that adhesive forces hold the sample on the end of the wire 82, especially after evaporation of the solvent.

Next, the reaction chamber wall 81 is slipped over the sample-bearing end of ferromagnetic wire 82 until reaction chamber wall 81 seats firmly in a rubber cap 78 around the end of wire holder 76. In this assembly, the same is disposed within one end of the elongated reaction chamber 80 at the first position therein.

The insertion probe/reaction chamber assembly is first inserted into the pyrolysis inlet 10 through insertion probe housing 16 at a position before the three-way vacuum valve within vacuum valve housing 18. With the insertion probe and sample at this position, the vacuum valve is positioned to allow evacuation of void 57 by the first vacuum pump, while simultaneously preventing communication between void 57 and voids 56a–d within the apparatus. A partial vacuum is thus created within reaction chamber 80 and all voids surrounding insertion probe 12. Simultaneously, voids 56a–d are continually kept evacuated through vacuum port 58 by a second vacuum pump located within the mass spectrometer. After all voids within the apparatus have been evacuated, the vacuum valve is repositioned to shut off communication between the first vacuum pump and void 57, while allowing communication between void 57 and voids 56a-d. In this position, the second vacuum pump connected to the mass spectrometer continues to evacuate voids 56a-d and 57.

With the interior of pyrolysis inlet 10 evacuated, insertion probe 12 is inserted further into the pyrolysis inlet 10 until end 60 of first telescoping member 11 rests against a wall stop 64 which prevents further movement of the first telescoping member. This is the position of insertion probe 12 illustrated in FIG. 2.

Beveled guide 88 facilitates movement of reaction chamber wall 81 through the apparatus to within heating mantle 94. In this position, the end of reaction chamber wall 81 is in direct contact with seat 98, and the sample-bearing end of ferromagnetic wire 82 is positioned at a first position within reaction chamber 80. A first portion of the reaction chamber wall 81 and reaction chamber 80 adjacent cooling reservoir 72 are cooled to keep the sample cool at the first position so that there is no premature pyrolyzing of the sample. While the sample is being cooled at the first position as shown in FIG. 2, a second (most forward) portion of the reaction chamber wall 81 and reaction chamber 80 enveloped within heating mantle 94 is heated by the heating mantle to a temperature selected between ambient and 500° C., depending on the type of analysis to be performed.

When the second portion of reaction chamber 80 has reached the desired temperature, the end of ferromagnetic wire 82 bearing the sample is introduced into the heated, second portion of the reaction chamber at a second position therein. This is accomplished by inserting probe shaft 14 further into pyrolysis inlet 10 until end 66 of second telescoping member 13 rests against wall stop 64. Beveled guide 90 assures smooth movement of second telescoping member 13 within the apparatus. As second telescoping member 13 is moved towards wall stop 64, spring 50 is compressed, thereby causing a repelling force between probe shaft 14 and first telescoping member 11. Head 46 of bolt 44 moves through the void 77 within first telescoping member 11 as second telescoping member 13 is moved towards wall stop 64. Correspondingly, the wire holder 76 which houses ferromagnetic wire 82 and which is mounted to the head 46 of support bolt 44 is further inserted into reaction chamber 80 until the sample-bearing end of ferromagnetic wire 82 is positioned within the heated portion of reaction chamber 80 at the second position therein.

Immediately after the sample-bearing end of ferromagnetic wire 82 is moved from the cooled, first position to the heated, second position within reaction chamber 80, the sample is rapidly pyrolyzed by quickly heating ferromagnetic wire 82. This is accomplished by introducing an electrical current through electrical feedthroughs 22 to energize high frequency coil 92, thereby emitting electromagnetic energy in the form of high frequency radio waves. The frequency of the radio waves emitted by high frequency coil 92 is generally kept within a range of several hundred thousand to several million cycles per second, empirically determined to provide high absorption below the Curie-point temperature and minimal absorption above this temperature for the alloys and dimensions of the most frequently used types of wires.

The high frequency radio waves emitted by coil 92 penetrate heating mantle 94 and reaction chamber wall 81 to enter the reaction chamber 80. A portion of the high frequency radio waves is absorbed by ferromagnetic wire 82 causing the wire to heat rapidly. The sample on the end of wire 82 is consequently heated quickly and is pyrolyzed into numerous volatile fragments. Pyrolysis of the sample in the second heated portion of reaction chamber 80 is generally accomplished within about 100 milliseconds to about six seconds, depending on the strength of the electromagnetic field.

The volatile pyrolysis products exit outlet 86—the only escape route from reaction chamber 80—and enter expansion chamber 102 through inlet port 100. Due to the heated nature of reaction chamber wall 81, condensation of less volatile pyrolysis products on reaction chamber wall 81 is substantially inhibited so that these components are introduced into the expansion chamber 102 together with the more volatile components. Moreover, since the sample is cooled at the first position within reaction chamber 80 immediately before being moved to the second position for pyrolysis, the sample experiences practically no thermal damage prior to pyrolysis; this prevents highly volatile components of the sample from escaping pyrolysis and subsequent entry into expansion chamber 102.

Expansion chamber 102 acts to retard the movement of the volatile pyrolysis products, allowing those sample components first entering expansion chamber 102 to mix with the later entering sample components. Thus, as the pyrolyzed components exit the expansion chamber 102 through outlet port 108 and enter the mass spectrometer for analysis, the exiting mixture contains representative portions of substantially all the pyrolysis components of the sample.

Expansion chamber wall 101 is made of such materials as stainless steel or borosilicate glass, with a gold-coating on the interior surface thereof, and is heated by heating element 106 within the expansion chamber wall 101. The heated, gold-plated interior of expansion chamber wall 101 substantially inhibits condensation and degradation of the volatile pyrolysis components on the expansion chamber wall 101.

Expansion chamber outlet port 108 is positioned directly in front of the ion source of the mass spectrometer for immediate mass spectrometric analysis of the pyrolysis products. Since virtually all of the sample components are present in the mixture analyzed by the mass spectrometer, the resultant mass spectrum provides an accurate fingerprint for both identifying the sample and constructively deducing the actual chemical structure of the sample.

The combination pyrolysis inlet/ass spectrometer of the present invention has been used to analyze an extensive range of materials heretofore impossible to characterize and identify by traditional analytical techniques. Following is a list of materials that can be fingerprinted using the pyrolysis/mass spectrometer of the present invention:

| Biological and Medical | Geochemical and Environmental | Industrial and Forensic |
|---|---|---|
| Biopolymers | Coals or Shale Tars | Plastics and Fibers |
| Microorganisms | Sediments | Coatings and Paints |
| Cells and Tissues | Humic Matter | Natural Products |
| Body Fluids | Sludges and Water | Vaccines and Drugs |
| Biochemical Fractions | Air Particulates | Foods and Drinks |

Exceptional reproducibility of consecutive mass spectra is obtained from the combination pyrolysis inlet/mass spectrometer due to the unique features of pyrolysis inlet 10. For example, by cooling and preheating the reaction chamber 80 at the first and second positions, respectively, pyrolysis component losses due to thermal damage prior to pyrolysis or condensation on reaction chamber wall 81 are substantially eliminated and each component of the original sample is preserved for final analysis by the mass spectrometer.

Another important factor in achieving reproducibility in the present invention is the vacuum conditions existing within reaction chamber 80 during pyrolysis of the sample. The relatively low pressure within reaction chamber 80 during pyrolysis helps to prevent condensation of low, volatile fragments. This ensures that substantially the entire chemical structure of the sample will be represented by the volatile fragments produced in each successive pyrolysis, the vacuum assisting in keeping even the high-boiling pyrolysis fragments in the gaseous state. In addition, the unique single loop configuration of heating mantle filament 96 minimizes induction interference of the heating mantle 94 with the electromagnetic energy emitted by high frequency coil 92 and absorbed by ferromagnetic wire 82. This design of the heating mantle 94 ensures that substantially the same temperature rise profile is achieved during each pyrolysis and that successive samples will be pyrolyzed at nearly the same maximum temperature, i.e., the Curie point of ferromagnetic wire 82.

Another advantage of the pyrolysis/mass spectrometric technique and apparatus disclosed herein is that large batches of samples can be prepared in advance since the entire process from insertion of the sample to completed mass spectrometric analysis generally takes less than two minutes. Additionally, contamination within the pyrolysis inlet 10 from one sample to the next is minimal since the walls of reaction chamber 80, expansion chamber 102, and the mass spectrometer inlet are all preheated to prevent condensation of low volatile pyrolysis fragments thereon. Thus, quick, reproducible data can be obtained from large batches of samples.

Contamination within the pyrolysis inlet 10 is further minimized by a simple procedure performed between analyses. After pyrolysis of one sample, insertion probe 12 is removed from pyrolysis inlet 10 and the ferromagnetic wire 82 is removed and replaced with a new ferromagnetic wire 82. Since ferromagnetic sampling wires are inexpensive, they are generally discarded after each pyrolysis. Reaction chamber 80 is also removed and replaced with a clean reaction chamber 80; used reaction chambers are easily flame-cleaned for reuse.

The result of using fresh ferromagnetic wires and cleaned reaction chambers is that "cross-talk" between samples is practically nonexistent. "Cross-talk" refers to the background interference appearing in subsequent mass spectra caused by contamination buildup within the pyrolysis inlet 10. Since contamination is substantially eliminated within the present invention, cross-talk no longer becomes a significant problem. In fact, contamination buildup in the pyrolysis inlet 10 is so minimal that literally thousands of samples may be analyzed without the need for cleaning the pyrolysis inlet 10 or the ion source of the mass spectrometer.

A still further advantage of the modular pyrolysis inlet 10 of the present invention is the incorporation of many different pyrolysis modes in the same apparatus. In addition to the heating mantle/high frequency coil heating mode described above, oven pyrolysis of a sample can be accomplished by employing heating mantle 94 alone to heat and chemically decompose the sample. In this mode, high frequency coil 92 is not activated, and as described below, the sample can be pyrolyzed by two different methods.

The first method consists of cooling the sample in the first portion of reaction chamber 80 while preheating the second portion of the reaction chamber 80 with heating mantle 94. When the second portion of the reaction chamber 80 is heated sufficiently, the sample is moved from the first position to the second position (within the heated, second portion of reaction chamber 80) for pyrolysis.

Alternatively, the sample can be introduced directly into the heated, second portion of the reaction chamber 80 before activation of the heating mantle 94. Heating mantle 94 is then activated so as to heat the sample gradually and cause the sample to pyrolyze over an extended period of time. This heating method is useful to make time studies of the pyrolysis components as they are released from the sample during pyrolysis. By gradually heating the sample, the mass spectrometer can analyze the products one at at time as they are released.

Pyrolysis of the sample within pyrolysis inlet 10 can also be accomplished by deactivating heating mantle 94 and using high frequency coil 92 along to pyrolyze the sample within reaction chamber 80. This heating mode is used especially where it is desirable to analyze only the more volatile components of the sample. Immediately after rapidly pyrolyzing the sample by energizing coil 92 to heat wire 82, the less volatile components of the pyrolysis products condense on the cold reaction chamber wall 81 while the more volatile components enter expansion chamber 102 through inlet 100, the more volatile components being subsequently analyzed by the mass spectrometer.

Still another method for pyrolyzing the sample within the pyrolysis inlet 10 is by irradiating the sample at the second position within reaction chamber 80 with a laser beam (not shown).

Advantageously, modular expansion chamber 102 can be removed from the pyrolysis inlet 10 for a direct probe analysis by removing the bolts 38 connecting flanges 34 and 36 and pulling flange 36 away from flange 34. With the expansion chamber 102 removed, outlet 86 of reaction chamber 80 is placed directly in front of the ion source of the mass spectrometer and pyrolysis products exiting reaction chamber 80 enter directly into the mass spectrometer for analysis without the delaying or mixing which would occur if an expansion chamber were used.

The direct probe analysis is especially useful to obtain time-resolved spectra of different components of the sample. By gradually heating the sample using the oven pyrolysis mode in a direct probe analysis, the rate of release of highly volatile pyrolysis products which tend to escape analysis by the mass spectrometer is minimized and the released pyrolysis components are analyzed immediately after they are released.

It will be readily appreciated that heating mantle 94 and high frequency coil 92 may be used in combination to pyrolyze the sample, as previously set forth, without the modular expansion chamber 102. Thus, modular pyrolysis inlet 10 offers a wide range of possibilities for different applications and purposes. For example, in the pyrolysis of extremely complex macromolecular materials, both high frequency coil 92 and heating mantle 94 may be used to ensure complete pyrolysis of the sample and minimize the loss of less volatile components of the complex structure. If much simpler compounds are to be analyzed, it may be desirable to perform a direct probe oven pyrolysis using heating mantle 94 to gradually pyrolyze the sample, introducing the pyrolysis products directly into the mass spectrometer to obtain time-resolved spectra of the material analyzed.

It becomes readily apparent that it would be difficult to discuss herein all of the various permutations of applications which are possible with the modular pyrolysis inlet 10 of the present invention. Advantageously, modular pyrolysis inlet 10 may be dismounted from the mass spectrometer for ordinary use of the mass spectrometer without pyrolysis of the sample to be analyzed. It will also be recognized that the modular pyrolysis inlet may be mounted to other instrumentation where pyrolysis of the sample before analysis is desirable. For example, pyrolysis inlet 10 may also be mounted to a combination mass spectrometer/mass spectrometer where identification of one selected ion species of the pyrolysis products is desired.

An alternative embodiment of the insertion probe/reaction chamber assembly of the present invention is shown in FIG. 4. In this embodiment, the insertion probe 12a has no telescoping feature as the insertion probe 12 of the embodiment of FIG. 2, and is much more simple in construction. A probe shaft 14a is formed with extension 13a and an end 60a, very similar to the probe shaft 14, second telescoping member 13, and end 60 of the insertion probe 12 of FIG. 2.

In this second preferred embodiment, reaction chamber wall 81a is configured with a reaction chamber 80a formed at one end and with a small recess at the other end for securing ferromagnetic wire 82a therein. Thus, reaction chamber wall 81a performs the function of both the sample wire holder 76 and the reaction chamber wall 81 of the embodiment depicted in FIG. 2. Reaction chamber wall 81a is secured to extension 13a by a rubber cap 78a which is held in place by threads 84a in the same way as rubber cap 78 of the first preferred embodiment.

Insertion of the insertion probe/reaction chamber assembly of the second preferred embodiment is accomplished in much the same manner as the first preferred embodiment of FIG. 2. Referring now to FIGS. 2 and 4, the insertion probe/reaction chamber assembly of FIG. 4 is inserted into probe shaft housing 16 for evacuation of reaction chamber 82a and surrounding void 57 by the first vacuum pump in communication with the vacuum valve within vacuum valve housing 18. After evacuation, the vacuum valve is repositioned to allow communication between void 57 and voids 56a–d.

The insertion probe/reaction chamber assembly of FIG. 4 is then further inserted into pyrolysis inlet 10 until end 60a meets wall stop 64. At this point, the sample-bearing end of ferromagnetic wire 82a is positioned within the heating mantle 94 of pyrolysis inlet 10. This embodiment thus eliminates the benefits obtained from the cooling feature of the first embodiment at the first position within reaction chamber 80.

When employing the second preferred embodiment of FIG. 4, it is generally desirable to pyrolyze the sample by energizing high frequency coil 92 without activating heating mantle 94. In this way, when the sample is pyrolyzed, the more volatile pyrolysis products exit outlet 86a and enter the mass spectrometer either directly or by route of expansion chamber 102, while the less volatile pyrolysis products condense on the relatively cold reaction chamber wall 81a. After mass spectrometric analysis of the more volatile pyrolysis components, the heating mantle is activated to vaporize the condensed components on reaction chamber wall 81a. These components then enter the mass spectrometer for analysis and a separate spectrum thereof is obtained. Since non-telescoping insertion probe 12a of the second preferred embodiment is of much simpler construction than its telescoping counterpart in the first embodiment, the benefits derived from the telescoping and cooling features are sacrificed.

It will be appreciated that variations of the foregoing description are possible. For example, the materials disclosed for the construction of the different components of modular pyrolysis inlet 10 are by way of example only, and are not to be considered as the only materials which may be used in the construction thereof. Obviously, any materials which exhibit the properties disclosed herein may be substituted therefor.

Accordingly, it will be recognized that the invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for pyrolyzing a sample prior to analysis by a mass spectrometer, comprising:
   an insertion probe for bearing the sample;
   a reaction chamber which is mounted to the insertion probe so as to encompass the sample;
   means for preheating at least a portion of the reaction chamber;
   means for rapidly heating the sample within the preheated portion of the reactant chamber sufficient to pyrolyze the sample, said means for rapidly heating the sample being independent of the preheating means; and
   an outlet formed in the reaction chamber to allow passage of the pyrolyzed sample into a mass spectrometer positioned adjacent the reaction chamber, said outlet being positioned so as to direct the pyrolyzed sample into the mass spectrometer while substantially prohibiting passage of the pyrolyzed sample into regions of the pyrolyzing apparatus outside of the reaction chamber.

2. An apparatus for pyrolyzing a sample as defined in claim 1 wherein the insertion probe comprises a wire, and wherein the means for rapidly heating the sample is an energy source capable of rapidly heating the wire.

3. An apparatus for pyrolyzing a sample as defined in claim 2 wherein the means for rapidly heating the sample is a coil capable of emitting electromagnetic energy, and wherein the wire is made of a ferromagnetic material capable of being heated through the absorption of at least a portion of the energy emitted by the coil.

4. An apparatus for pyrolyzing a sample as defined in claim 3 wherein the reaction chamber preheating means is positioned between the reaction chamber and the coil.

5. An apparatus for pyrolyzing a sample as defined in claim 4 wherein the reaction chamber preheating means is formed from a single loop of wire such that it does not substantially interfere with the absorption of electromagnetic energy by the ferromagnetic wire.

6. An apparatus for pyrolyzing a sample as defined in claim 1 wherein the insertion probe is telescopically movable such that the sample may be positioned at a first position outside that portion of the reaction chamber which is preheated and at a second position within that portion of the reaction chamber which is preheated.

7. An apparatus for pyrolyzing a sample as defined in claim 6 further comprising means for cooling the sample at the first position.

8. An apparatus for pyrolyzing a sample as defined in claim 1 further comprising an expansion chamber positionned between and providing gaseous communication between the outlet of the reaction chamber and the mass spectrometer during pyrolysis of the sample.

9. An apparatus for pyrolyzing a sample as defined in claim 8 further comprising means for heating the expansion chamber.

10. An apparatus for pyrolyzing a sample prior to analysis by a mass spectrometer, comprising:
an insertion probe for bearing the sample;
a reaction chamber which is mounted to the insertion probe so as to encompass the sample;
means for heating the sample within the reaction chamber sufficient to pyrolyze the sample, the insertion probe being telescopically movable so as to permit first positioning of the sample outside the heating means and second positioning of the sample adjacent the heating means; and
an outlet formed in the reaction chamber to allow passage of the pyrolyzed sample into a mass spectrometer positioned adjacent the reaction chamber, said outlet being positioned so as to direct the pyrolyzed sample into the mass spectrometer while substantially prohibiting passage of the pyrolyzed sample into regions of the pyrolyzing apparatus outside of the reaction chamber.

11. An apparatus for pyrolyzing a sample as defined in claim 10 further comprising means for cooling the sample at the first position.

12. An apparatus for pyrolyzing a sample as defined in claim 11 wherein the insertion probe comprises a wire, and wherein the heating means further comprises an energy source capable of rapidly heating the wire.

13. An apparatus for pyrolyzing a sample as defined in claim 12 wherein the energy source is a coil capable of emitting electromagnetic energy, and wherein the wire is made of a ferromagnetic material capable of being heated through the absorption of at least a portion of the energy emitted by the coil.

14. An apparatus for pyrolyzing a sample as defined in claim 13 wherein the heating means is positionned between the reaction chamber and the coil.

15. An apparatus for pyrolyzing a sample as defined in claim 14 wherein the heating means has a heating element which does not substantially interfere with the absorption of electromagnetic energy by the ferromagnetic wire.

16. An apparatus for pyrolyzing a sample as defined in claim 10 further comprising an expansion chamber positioned between and providing gaseous communication between the outlet of the reaction chamber and the mass spectrometer during pyrolysis of the sample.

17. An apparatus for pyrolyzing a sample as defined in claim 16 further comprising means for heating the expansion chamber.

18. An apparatus for analyzing a sample comprising:
an insertion probe for bearing the sample;
a reaction chamber which is mounted to the insertion probe so as to encompass the sample;
means for preheating at least a portion of the reaction chamber, the insertion probe being telescopically movable such that the sample may be positioned at a first position outside that portion of the reaction chamber which is preheated and at a second position within that portion of the reaction chamber which is preheated;
means for cooling the sample at the first position;
means for rapidly heating the sample sufficient to pyrolyze the sample at the second position within the preheated portion of the reaction chamber, said means for rapidly heating the sample being independent of the preheating means; and
an outlet formed in the reaction chamber to allow passage of the pyrolyzed sample into a mass spectrometer positioned adjacent the reaction chamber, said outlet being positioned so as to direct the pyrolyzed sample into the mass spectrometer while substantially prohibiting passage of the pyrolyzed sample into regions of the analyzing apparatus outside of the reaction chamber.

19. An apparatus for analyzing a sample as defined in claim 18 further comprising:
an expansion chamber positioned between and providing gaseous communication between the outlet of the reaction chamber and the mass spectrometer during pyrolysis of the sample; and
means for heating the expansion chamber.

20. An apparatus for analyzing a sample comprising:
an insertion probe having a ferromagnetic wire for bearing the sample;
a reaction chamber which is mounted to the insertion probe so as to encompass the wire and sample;
means for creating a partial vacuum within the reaction chamber;
means for cooling the sample at a first position within the apparatus;
means for heating the reaction chamber at a second position within the apparatus, the insertion probe being telescopically movable so as to permit selective positioning of the sample at the first and second positions;
means for transmitting electromagnetic energy to the ferromagnetic wire so as to heat the wire and pyrolyze the sample within the reaction chamber at the second position; and
an outlet formed in the reaction chamber to allow passage of the pyrolyzed sample into a mass spectrometer positioned adjacent the reaction chamber, said outlet being positioned so as to direct the pyrolyzed sample into the mass spectrometer while substantially prohibiting passage of the pyrolyzed sample into regions of the analyzing apparatus outside of the reaction chamber.

21. An apparatus for pyrolyzing a sample as defined in claim 20 further comprising an expansion chamber removably positioned between the outlet of the reaction chamber and the mass spectrometer when the sample is at the second position.

22. A method for analyzing a sample comprising the steps of:
preheating at least a portion of a reaction chamber;
introducing the sample into the preheated portion of the reaction chamber;

rapidly heating the sample within the preheated portion of the reaction chamber so as to pyrolyze the sample, the rapid heating of the sample being achieved independently of the preheating of the reaction chamber; and allowing passage of the pyrolyzed sample from the reaction chamber into a mass spectrometer while substantially prohibiting passage of the pyrolyzed sample into regions outside of the reaction chamber and the mass spectrometer.

23. A method for analyzing a sample as defined in claim 22 further comprising the step of cooling a portion of the reaction chamber and positioning the sample within the cool portion of the reaction chamber prior to introduction of the sample into the preheated portion of the reaction chamber.

24. A method for analyzing a sample as defined in claim 22 further comprising the step of delaying passage of the pyrolyzed sample into the mass spectrometer.

25. A method for analyzing a sample comprising the steps of:

securing a wire to the end of an insertion probe, the insertion probe being telescopically movable so as to permit variable positioning of the wire;

placing the sample on the wire;

introducing the wire and sample into a reaction chamber at a first position therein and securing the reaction chamber to the insertion probe;

cooling the sample at the first position;

moving the insertion probe so as to introduce the sample at a second position within the reaction chamber;

heating the sample at the second position so as to pyrolyze the sample; and allowing passage of the pyrolyzed sample from the reaction chamber into a mass spectrometer while substantially prohibiting passage of the pyrolyzed sample into regions outside of the reaction chamber and the mass spectrometer.

26. A method for analyzing a sample as defined in claim 25 further comprising the step of preheating a portion of the reaction chamber adjacent the second position of the sample prior to moving the sample to the second position.

27. A method for analyzing a sample as defined in claim 25 further comprising the step of preventing gaseous components of the pyrolyzed sample from condensing in the reaction chamber.

28. A method for analyzing a sample as defined in claim 25 further comprising the step of delaying passage of the pyrolyzed sample into the mass spectrometer.

29. A method for analyzing a sample comprising the steps of:

securing a wire capable of being rapidly heated to the end of an insertion probe, the insertion probe being telescopically movable so as to permit variable positioning of the wire;

placing the sample on the wire;

introducing the wire and sample into a reaction chamber at a first position therein and securing the reaction chamber to the insertion probe;

cooling a first portion of the reaction chamber at the first position;

preheating a second portion of the reaction chamber at a second position therein;

moving the insertion probe so as to introduce the wire and sample into the preheated portion of the reaction chamber at the second position;

rapidly heating the wire within the preheated portion of the reaction chamber at the second position so as to pyrolyze the sample, the rapid heating of the sample being achieved independently of the preheating of the second portion of the reaction chamber; and allowing passage of the pyrolyzed sample from the reaction chamber into a mass spectrometer while substantially prohibiting passage of the pyrolyzed sample into regions outside of the reaction chamber and the mass spectrometer.

30. An apparatus for pyrolyzing a sample as defined in claim 1 wherein the reaction chamber is replaceable.

31. An apparatus for pyrolyzing a sample as defined in claim 2 wherein the wire is replaceable.

32. An apparatus for pyrolyzing a sample as defined in claim 1 wherein the preheating means is capable of preheating the portion of the reaction chamber to be preheated to a temperature of up to about 500° C. and wherein the means for rapidly heating the sample is capable of heating the sample to a temperature within the range of about 358° C. to about 1128° C.

33. An apparatus for pyrolyzing a sample as defined in claim 10 wherein the reaction chamber is replaceable.

34. An apparatus for pyrolyzing a sample as defined in claim 12 wherein the wire is replaceable.

35. An apparatus for analyzing a sample as defined in claim 20 wherein the ferromagnetic wire and the reaction chamber are replaceable.

36. A method for analyzing a sample as defined in claim 22 further comprising the step of replacing the reaction chamber after pyrolysis of the sample with a clean reaction chamber so as to provide a clean environment for subsequent analyses.

37. A method for analyzing a sample as defined in claim 22 wherein the preheated portion of the reaction chamber is at a temperature of up to about 500° C. and wherein the sample is rapidly heated to a temperature within the range of about 358° C. to about 1128° C. within the preheated portion of the reaction chamber.

38. A method for analyzing a sample as defined in claim 25 further comprising the step of replacing the wire and the reaction chamber after pyrolysis of the sample with a clean wire and a clean reaction chamber so as to provide a clean environment for subsequent analyses.

39. A method for analyzing a sample as defined in claim 29 further comprising the step of replacing the wire and the reaction chamber after pyrolysis of the sample with a clean wire and a clean reaction chamber so as to provide a clean environment for subsequent analyses.

* * * * *

UNITED STATES PATENT AND TRADEMARK OFFICE
CERTIFICATE OF CORRECTION

PATENT NO. : 4,408,125
DATED : October 4, 1983
INVENTOR(S) : Hendrik L. C. Meuzelaar It is certified that error appears in the above—identified patent and that said Letters Patent is hereby corrected as shown below:

Column 1, line 66, "Curie point" should be --Curie-point--

Column 5, line 63, "simlar" should be --similar--

Column 7, line 14, "Curiepoint" should be Curie-point--

Column 10, line 50, "pyrolysis inlet/ass spectrometer"
        should be --pyrolysis inlet/mass spectrometer--

Column 11, line 27 and 28, "Curie point" should be
                --Curie-point--

Column 14, line 41, "reactant chamber" should be
                --reaction chamber--

Signed and Sealed this

Thirteenth Day of December 1983

[SEAL]

Attest:

GERALD J. MOSSINGHOFF

Attesting Officer      Commissioner of Patents and Trademarks